United States Patent
Ogata et al.

(10) Patent No.: US 11,147,575 B2
(45) Date of Patent: Oct. 19, 2021

(54) HYDRAULIC FORCEPS SYSTEM

(71) Applicant: KAWASAKI JUKOGYO KABUSHIKI KAISHA, Kobe (JP)

(72) Inventors: Mariko Ogata, Kobe (JP); Hideki Tanaka, Nishinomiya (JP); Tetsuya Nakanishi, Nishinomiya (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 244 days.

(21) Appl. No.: 16/474,259

(22) PCT Filed: Dec. 20, 2017

(86) PCT No.: PCT/JP2017/045659
§ 371 (c)(1),
(2) Date: Jun. 27, 2019

(87) PCT Pub. No.: WO2018/123754
PCT Pub. Date: Jul. 5, 2018

(65) Prior Publication Data
US 2020/0121341 A1    Apr. 23, 2020

(30) Foreign Application Priority Data
Dec. 27, 2016 (JP) ............... JP2016-252569

(51) Int. Cl.
| A61B 17/28 | (2006.01) |
| A61B 34/30 | (2016.01) |
| A61B 34/37 | (2016.01) |
| A61B 17/29 | (2006.01) |

(Continued)

(52) U.S. Cl.
CPC ............ *A61B 17/28* (2013.01); *A61B 17/29* (2013.01); *A61B 34/30* (2016.02); *A61B 34/37* (2016.02); *B25J 15/08* (2013.01); *A61B 2017/00119* (2013.01); *A61B 2017/00539* (2013.01); *A61B 2034/302* (2016.02)

(58) Field of Classification Search
CPC .......... A61B 17/28; A61B 17/29; A61B 2017/00539; A61B 2017/2912; A61B 2017/2932
See application file for complete search history.

(56) References Cited

U.S. PATENT DOCUMENTS

| 4,848,338 A | * | 7/1989 | De Satnick | ............ | A61B 17/29 606/1 |
| 5,250,074 A | * | 10/1993 | Wilk | ............... | A61B 17/12 606/158 |

(Continued)

FOREIGN PATENT DOCUMENTS

| JP | S63-160631 A | 7/1988 |
| JP | 2002-253574 A | 9/2002 |

(Continued)

*Primary Examiner* — Ryan J. Severson
(74) *Attorney, Agent, or Firm* — Oliff PLC

(57) ABSTRACT

A hydraulic forceps system includes: robotic forceps whose gripper is opened and closed by utilizing hydraulic pressure of a hydraulic fluid; a pressure sensor that detects a pressure of the hydraulic fluid; and a control device that calculates a current gripping force of the gripper based on the pressure of the hydraulic fluid detected by the pressure sensor; and a monitor that displays the current gripping force.

10 Claims, 4 Drawing Sheets

(51) Int. Cl.
*B25J 15/08* (2006.01)
*A61B 17/00* (2006.01)

(56) References Cited

U.S. PATENT DOCUMENTS

| | | | | |
|---|---|---|---|---|
| 5,720,742 A * | 2/1998 | Zacharias | | A61B 17/29 |
| | | | | 606/1 |
| 5,791,231 A * | 8/1998 | Cohn | | B25J 9/144 |
| | | | | 606/1 |
| 5,833,656 A * | 11/1998 | Smith | | B25J 3/04 |
| | | | | 604/95.01 |
| 7,559,452 B2 * | 7/2009 | Wales | | A61B 17/068 |
| | | | | 227/175.1 |
| 8,114,122 B2 * | 2/2012 | Nau, Jr. | | A61B 18/1445 |
| | | | | 606/207 |
| 8,241,228 B1 * | 8/2012 | Cohen | | A61B 17/3201 |
| | | | | 600/573 |
| 8,594,841 B2 * | 11/2013 | Zhao | | A61B 34/37 |
| | | | | 700/245 |
| 8,746,533 B2 * | 6/2014 | Whitman | | A61B 17/07207 |
| | | | | 227/176.1 |
| 9,133,864 B2 * | 9/2015 | Menon | | B25J 9/142 |
| 9,149,338 B2 * | 10/2015 | Ko | | A61B 34/76 |
| 9,675,418 B2 * | 6/2017 | Doyle | | F15B 7/00 |
| 9,808,317 B2 * | 11/2017 | Marczyk | | A61B 17/3423 |
| 9,814,480 B2 * | 11/2017 | Tadano | | A61B 34/71 |
| 2006/0235368 A1 * | 10/2006 | Oz | | A61B 17/29 |
| | | | | 606/1 |
| 2010/0069953 A1 * | 3/2010 | Cunningham | | A61B 17/29 |
| | | | | 606/208 |
| 2010/0169815 A1 | 7/2010 | Zhao et al. | | |
| 2010/0331879 A1 * | 12/2010 | Harris | | A61B 17/29 |
| | | | | 606/205 |
| 2011/0106141 A1 | 5/2011 | Nakamura | | |
| 2013/0138118 A1 | 5/2013 | Doyle | | |
| 2014/0330073 A1 | 11/2014 | Ko et al. | | |
| 2015/0313619 A1 | 11/2015 | Tadano et al. | | |
| 2016/0030071 A1 * | 2/2016 | Ichikawa | | A61B 18/1445 |
| | | | | 606/41 |
| 2019/0314982 A1 * | 10/2019 | Kuribayashi | | B25J 15/0206 |
| 2019/0345959 A1 * | 11/2019 | Tanaka | | B25J 9/144 |
| 2020/0121341 A1 * | 4/2020 | Ogata | | A61B 17/29 |

FOREIGN PATENT DOCUMENTS

| | | |
|---|---|---|
| JP | 2003-039370 A | 2/2003 |
| JP | 2013-517898 A | 5/2013 |
| WO | 2004/028585 A2 | 4/2004 |

* cited by examiner $$X = \begin{bmatrix} x_1 \\ x_2 \\ \dot{x}_1 \\ \dot{x}_2 \\ P \end{bmatrix} \quad \dot{X} = \begin{bmatrix} \dot{x}_1 \\ \dot{x}_2 \\ \ddot{x}_1 \\ \ddot{x}_2 \\ \dot{P} \end{bmatrix} \quad Y = \begin{bmatrix} x_2 \\ P \end{bmatrix}$$

HYDRAULIC FORCEPS SYSTEM

TECHNICAL FIELD

The present invention relates to a hydraulic forceps system including robotic forceps whose gripper is opened and closed by utilizing hydraulic pressure.

BACKGROUND ART

Conventionally, robotic forceps have been used in, for example, endoscopic surgery. For example, Patent Literature 1 discloses robotic forceps whose gripper is opened and closed by utilizing hydraulic pressure. The robotic forceps of Patent Literature 1 are operated manually.

CITATION LIST

Patent Literature

PTL 1: Japanese Laid-Open Patent Application Publication No. S63-160631

SUMMARY OF INVENTION

Technical Problem

Assuming a situation where a doctor uses robotic forceps, while the doctor is operating the robotic forceps, when the gripper grips an affected part of a patient, it is difficult for the doctor to know how strong the gripping force is. This problem tends to be more prominent particularly in a case where the doctor operates robotic forceps equipped with a built-in motor by remote control.

In view of the above, an object of the present invention is to make it possible to show the current gripping force of the gripper to the doctor operating the robotic forceps.

Solution to Problem

In order to solve the above-described problems, the present invention provides a hydraulic forceps system including: robotic forceps whose gripper is opened and closed by utilizing hydraulic pressure of a hydraulic fluid; a pressure sensor that detects a pressure of the hydraulic fluid; and a control device that calculates a current gripping force of the gripper based on the pressure of the hydraulic fluid detected by the pressure sensor; and a monitor that displays the current gripping force.

According to the above configuration, the current gripping force of the gripper can be shown to a doctor operating the robotic forceps.

For example, the monitor may display the current gripping force together with an image of an inside of a body of a patient.

The robotic forceps may include: a first piston coupled to the gripper; a first cylinder accommodating the first piston and forming a first pressure chamber together with the first piston, the first pressure chamber being filled with the hydraulic fluid; a second piston; a second cylinder accommodating the second piston and forming a second pressure chamber together with the second piston, the second pressure chamber being filled with the hydraulic fluid; a communication passage through which the first pressure chamber and the second pressure chamber communicate with each other; and a motor that drives the second piston via a linear motion mechanism. The above hydraulic forceps system may further include a position sensor used for detecting a position of the second piston. The control device may include: an observer that derives an estimated position of the first piston based on the pressure of the hydraulic fluid detected by the pressure sensor and the position of the second piston detected by using the position sensor; and a gripping force calculator that calculates the current gripping force based on the estimated position of the first piston and the pressure of the hydraulic fluid detected by the pressure sensor. This configuration makes it possible to calculate the current gripping force of the gripper by taking into account the position of the first piston without installing a position sensor at the distal end portions of the robotic forceps.

The gripping force calculator may: calculate a theoretical gripping force from the pressure of the hydraulic fluid detected by the pressure sensor; calculate a friction force of a sealing member disposed between the first piston and the first cylinder from the estimated position of the first piston and the pressure of the hydraulic fluid detected by the pressure sensor; and calculate an estimated gripping force by subtracting the friction force of the sealing member from the theoretical gripping force. According to this configuration, the estimated gripping force can be calculated by taking into account the friction force of the sealing member disposed between the first piston and the first cylinder.

The gripping force calculator may calculate the current gripping force by correcting the estimated gripping force in accordance with an orientation of the robotic forceps. According to this configuration, the current gripping force can be calculated by taking into account the orientation of the robotic forceps.

The control device may include an alarm displayer that displays an alarm on the monitor when the current gripping force exceeds a threshold. This configuration makes it possible to let the doctor know immediately when the gripping force of the gripper has reached a dangerous level.

Advantageous Effects of Invention

The present invention makes it possible to show the current gripping force of the gripper to the doctor operating the robotic forceps.

DESCRIPTION OF EMBODIMENTS

Figure 1:
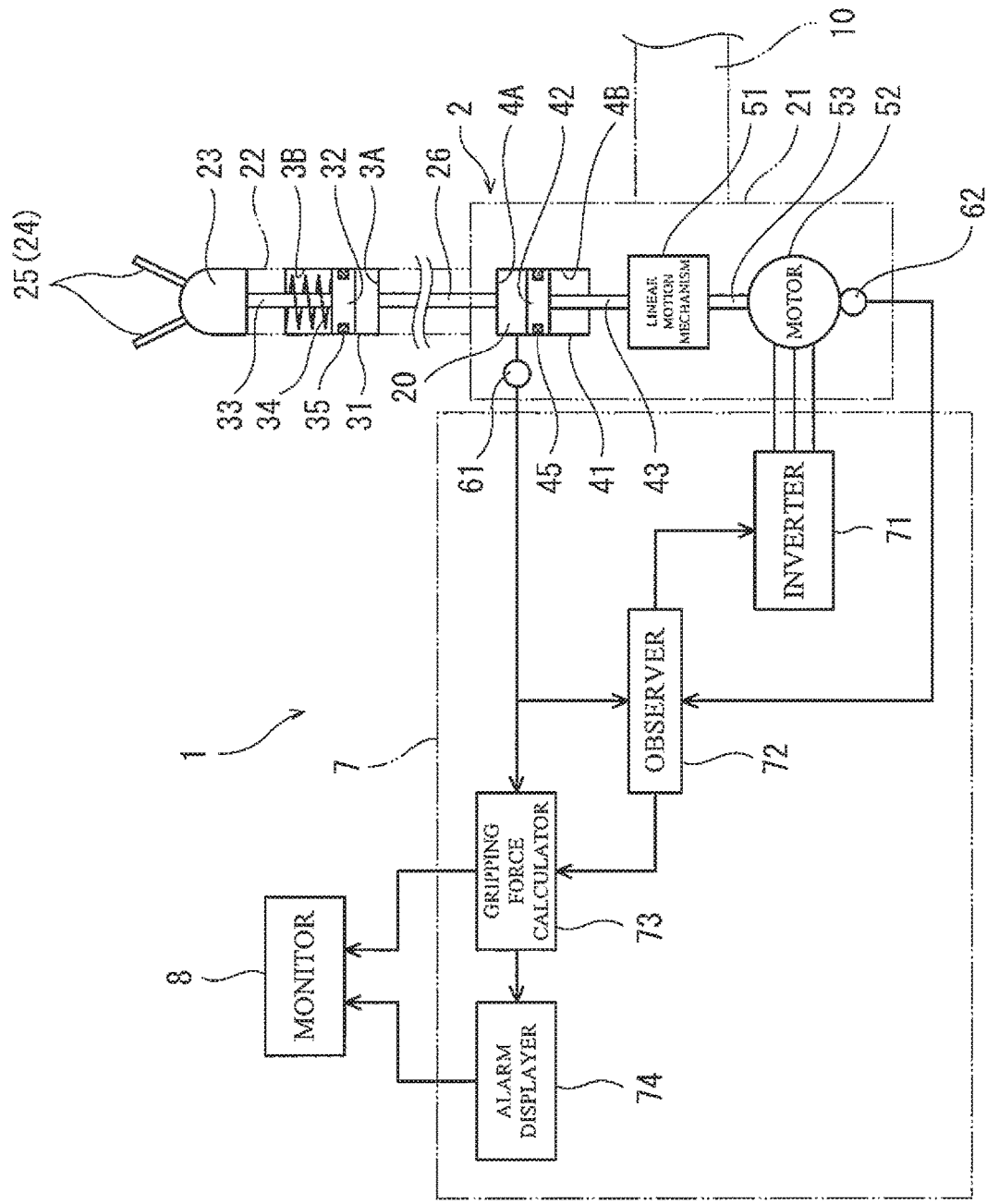
FIG. 1 shows a schematic configuration of a hydraulic forceps system according to one embodiment of the present invention.

FIG. 1 shows a hydraulic forceps system 1 according to one embodiment of the present invention. The hydraulic forceps system 1 includes robotic forceps 2, a control device 7, and a monitor 8.

In the present embodiment, the hydraulic forceps system 1 is used in a surgery assisting robot. Accordingly, the robotic forceps 2 are attached to a manipulator 10 of a slave device, and a doctor operates the robotic forceps 2 by remote control using a master device. The monitor 8 is incorporated in the master device. The control device 7 may be mounted in the master device or in the slave device. Alternatively, the control device 7 may be incorporated in a drive unit 21 of the robotic forceps 2. The drive unit 21 will be described below.

The manipulator 10 is an articulated robot capable of freely changing the orientation of the robotic forceps 2 while using a hole formed in the skin of a patient as a pivot for the movement of the robotic forceps 2.

The robotic forceps 2 include a gripper 24, which is opened and closed by utilizing the hydraulic pressure of a hydraulic fluid 20. The hydraulic fluid 20 is not limited to a particular type of fluid, but may be a saline solution or oil, for example.

Specifically, the robotic forceps 2 include: the drive unit 21; an insertion shaft 22 extending from the drive unit 21 and inserted in the body of the patient; and the gripper 24 provided at the distal end of the insertion shaft 22 and formed by a pair of tips 25. Although not illustrated, a mechanism that slides the insertion shaft 22 in its axial direction, and a mechanism that rotates the insertion shaft 22 about its central axis, may be incorporated in the drive unit 21. The insertion shaft 22 may be configured such that the distal end portion thereof is swingable, and a mechanism that swings the distal end portion of the insertion shaft 22 may be incorporated in the drive unit 21.

In the present embodiment, the insertion shaft 22 is a straight tube with high rigidity. However, as an alternative, the insertion shaft 22 may be a flexible tube.

A first cylinder 31 is disposed in the distal end portion of the insertion shaft 22. In the present embodiment, the central axis of the first cylinder 31 coincides with the central axis of the insertion shaft 22. The first cylinder 31 includes: a tubular portion; a front wall that blocks the inside of the tubular portion from the gripper 24 side; and a rear wall that blocks the inside of the tubular portion from the side opposite to the gripper 24 side.

A first piston 32 is accommodated in the first cylinder 31. A sealing member 35 is attached to the outer peripheral surface of the first piston 32. The sealing member 35 seals between the outer peripheral surface of the first piston 32 and the inner peripheral surface of the tubular portion of the first cylinder 31. A first pressure chamber 3A is formed between the first piston 32 and the rear wall of the first cylinder 31, and a back pressure chamber 3B is formed between the first piston 32 and the front wall of the first cylinder 31. The inside of the first pressure chamber 3A is filled with the hydraulic fluid 20, and the inside of the back pressure chamber 3B is open to the atmosphere. In the present embodiment, a spring 34, which urges the first piston 32, is disposed in the back pressure chamber 3B.

The first piston 32 is coupled to the gripper 24 by a rod 33 via a link mechanism 23. The rod 33 penetrates the front wall of the first cylinder 31. The link mechanism 23 converts linear motion of the rod 33 into opening/closing motion of the gripper 24.

A second cylinder 41, which is connected to the first cylinder 31 by a communication passage 26, is disposed in the drive unit 21. In the present embodiment, the axial direction of the second cylinder 41 is parallel to the axial direction of the insertion shaft 22. However, the axial direction of the second cylinder 41 is not particularly limited. The second cylinder 41 includes: a tubular portion; a front wall that blocks the inside of the tubular portion from the insertion shaft 22 side; and a rear wall that blocks the inside of the tubular portion from the side opposite to the insertion shaft 22 side.

A second piston 42 is accommodated in the second cylinder 41. A sealing member 45 is attached to the outer peripheral surface of the second piston 42. The sealing member 45 seals between the outer peripheral surface of the second piston 42 and the inner peripheral surface of the tubular portion of the second cylinder 41. A second pressure chamber 4A is formed between the second piston 42 and the front wall of the second cylinder 41, and a back pressure chamber 4B is formed between the second piston 42 and the rear wall of the second cylinder 41. The inside of the second pressure chamber 4A is filled with the hydraulic fluid 20, and the inside of the back pressure chamber 4B is open to the atmosphere.

The aforementioned communication passage 26 extends through the inside of the insertion shaft 22, and the first pressure chamber 3A and the second pressure chamber 4A communicate with each other through the communication passage 26. The inside of the communication passage 26 is also filled with the hydraulic fluid 20. For example, the communication passage 26 is formed by a metal tube or a flexible resin tube.

The second piston 42 is coupled to a linear motion mechanism 51 by a rod 43, which penetrates the rear wall of the second cylinder 41. The linear motion mechanism 51 is coupled also to an output shaft 53 of a motor 52. The linear motion mechanism 51 converts rotational motion of the output shaft 53 of the motor 52 into linear motion of the rod 43. That is, the motor 52 drives the second piston 42 via the linear motion mechanism 51 and the rod 43. The motor 52 is, for example, a servomotor.

When the second piston 42 moves forward as a result of the motor 52 rotating in one direction, the hydraulic fluid 20 is supplied from the second pressure chamber 4A to the first pressure chamber 3A, and thereby the first piston 32 moves forward against the urging force of the spring 34. On the other hand, when the second piston 42 moves rearward as a result of the motor 52 rotating in the reverse direction, the urging force of the spring 34 causes the first piston 32 to move rearward, and thereby the hydraulic fluid 20 is discharged from the first pressure chamber 3A to the second pressure chamber 4A. That is, the second cylinder 41, the second piston 42, the linear motion mechanism 51, and the motor 52 form a hydraulic fluid supply/discharge mechanism that supplies and discharges the hydraulic fluid to and from the first pressure chamber 3A.

The control device 7 controls the motor 52 based on a gripper opening/closing operation that is performed by using the aforementioned master device. The control device 7 includes, for example, a CPU and memories such as a ROM and RAM. The CPU executes a program stored in the ROM. Specifically, the control device 7 includes an inverter 71 and an observer 72. The control device 7 may be a single device, or may be divided into a plurality of devices.

In the present embodiment, the control device 7 is electrically connected to a pressure sensor 61 and a position sensor 62. The pressure sensor 61 detects the pressure P of the hydraulic fluid 20. The position sensor 62 is used for detecting the position $x_2$ of the second piston 42.

In the present embodiment, the position sensor 62 is a rotary encoder provided on the motor 52. The position sensor 62 detects the rotational displacement of the motor 52, and converts the rotational displacement into the position $x_2$ of the second piston 42. Alternatively, the position sensor 62 may be a linear encoder provided on the linear motion mechanism 51. Further alternatively, the position sensor 62 may be provided on the second cylinder 41, and may directly detect the position $x_2$ of the second piston 42.

Figures 2, 3:
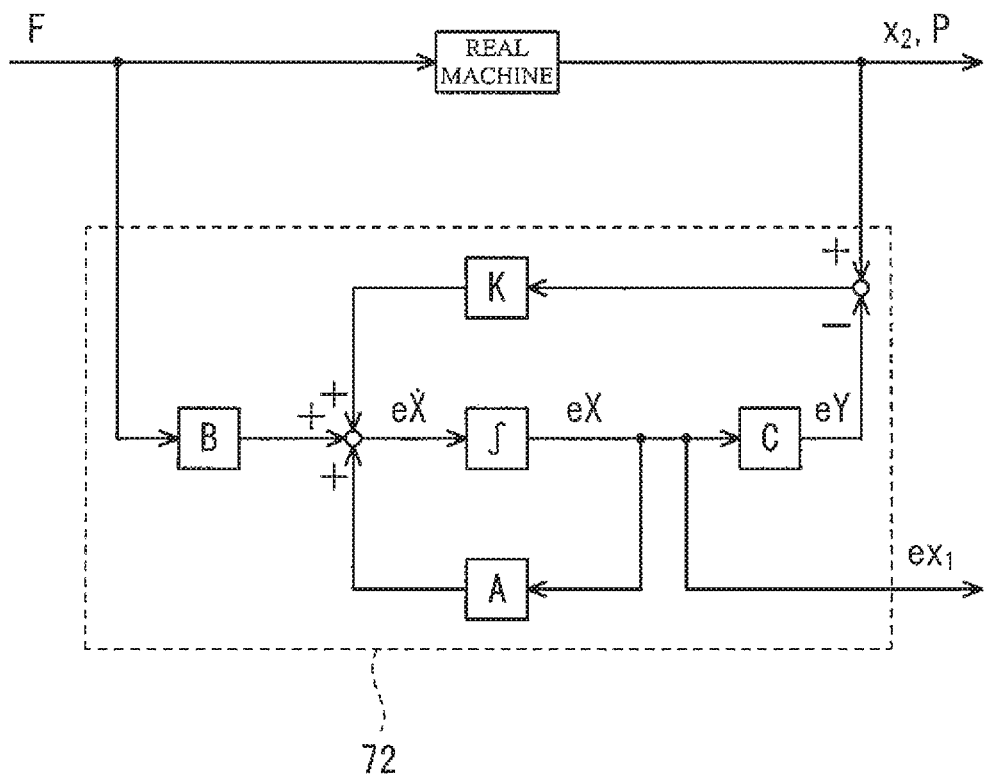
FIG. 2 is a block diagram of an observer.
FIG. 3 shows matrixes representing state parameters.

The observer 72 derives an estimated position $ex_1$ of the first piston 32 based on the pressure P of the hydraulic fluid 20 detected by the pressure sensor 61 and the position $x_2$ of the second piston 42 detected by using the position sensor 62. As shown in FIG. 2, the observer 72 is the modeling of a moving amount of the second piston 42 and a moving amount of the first piston 32 when a force F is applied to the second piston 42. The observer 72 can be represented by a state equation 1 and an output equation 2 shown below. It should be noted that, in the description below, a dot symbol that should be placed above a parameter according to Newton's notation is placed on the upper right of the parameter.

$$X'=AX+BF \quad (1)$$

$$Y=CX \quad (2)$$

X', X, Y: state parameters represented by matrixes shown in FIG. 3
$x_1$: position of the first piston
$x_2$: position of the second piston
P: pressure of the hydraulic fluid
F: force applied to the second piston
A, B: matrixes each representing a coefficient in the state equation 1
C: matrix representing a coefficient in the output equation 2

The matrixes A and B are obtained from, for example, a state equation relating to the first piston 32 and a state equation relating to the second piston 42.

To be more specific, the observer 72 first uses the matrixes A and B to obtain an estimated state parameter eX', and then integrates the estimated state parameter eX' to calculate an estimated state parameter eX. That is, the observer 72 derives not only the estimated position $ex_1$ of the first piston 32, but also an estimated position $ex_2$ of the second piston 42 and an estimated pressure eP of the hydraulic fluid 20.

Further, the observer 72 uses the matrix C to extract the estimated position $ex_2$ of the second piston 42 and the estimated pressure eP of the hydraulic fluid 20, and compares them with the position $x_2$ of the second piston 42 detected by using the position sensor 62 and the pressure P of the hydraulic fluid 20 detected by the pressure sensor 61. Then, the observer 72 uses a matrix K to calculate estimated errors for all the elements of the state parameter X' based on a deviation $\Delta x_e$ ($=x_2-ex_2$) between the detected position $x_2$ and the estimated position $ex_2$ of the second piston 42 and a deviation $\Delta P$ ($=P-eP$) between the detected pressure P and the estimated pressure eP of the hydraulic fluid 20. Thereafter, the observer 72 feeds back the calculated estimated errors to the calculation of the estimated state parameter eX'. In other words, the estimated errors are fed back to the deriving of the estimated position $ex_1$ of the first piston 32.

The inverter 71 supplies electric power to the motor 52, such that the estimated position $ex_1$ of the first piston 32 derived by the observer 72 is a command position for the first piston 32, the command position being based on a gripper opening/closing operation performed by using the master device.

Further, in the present embodiment, the control device 7 calculates the current gripping force Fc of the gripper 24 based on the pressure P of the hydraulic fluid 20 detected by the pressure sensor 61 and the position $x_2$ of the second piston 42 detected by using the position sensor 62. Specifically, the control device 7 includes a gripping force calculator 73 and an alarm displayer 74 in addition to the inverter 71 and the observer 72.

The gripping force calculator 73 calculates the current gripping force Fc based on the pressure P of the hydraulic fluid 20 detected by the pressure sensor 61 and the estimated position $ex_1$ of the first piston 32 derived by the observer 72.

Figure 4:
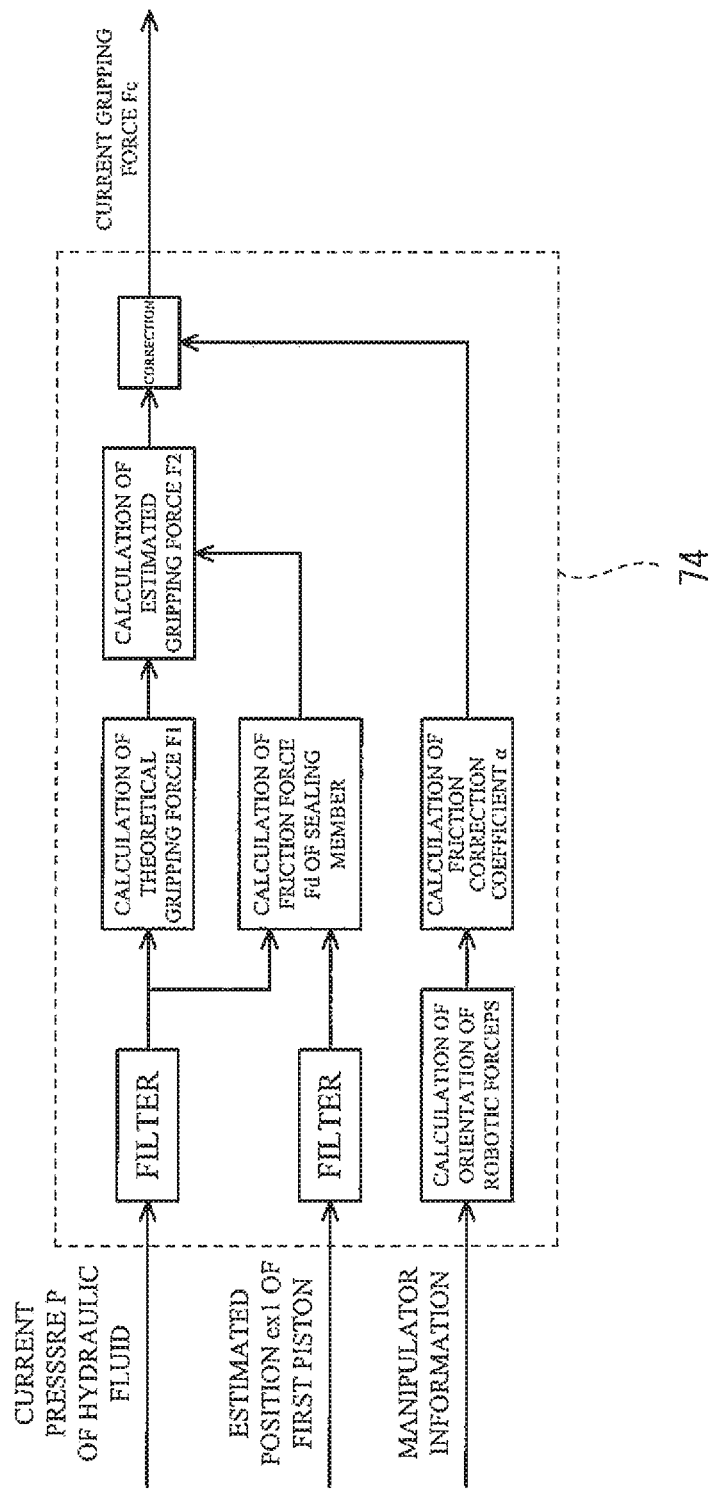
FIG. 4 is a block diagram of a gripping force calculator.

To be more specific, as shown in FIG. 4, the gripping force calculator 73 first calculates a theoretical gripping force F1 from the pressure P (in the present embodiment, pressure P' after being filtered) of the hydraulic fluid 20 detected by the pressure sensor 61. The theoretical gripping force F1 is calculated by using, for example, an equation shown below.

$$F1=A1 \times P' \times \beta$$

A1: area of the first piston
β: lever ratio of the gripper

The gripping force calculator 73 also calculates a friction force Fd of the sealing member 35 disposed between the first piston 32 and the first cylinder 31 from the estimated position $ex_1$ of the first piston 32 and the pressure P (in the present embodiment, pressure P' after being filtered) of the hydraulic fluid 20 detected by the pressure sensor 61. For example, test data indicating a relationship among the pressure P of the hydraulic fluid 20, the position $x_1$ of the first piston 32, and the friction force Fd of the sealing member 35 is prestored as a table in the memory of the control device 7, and the table is used for calculating the friction force Fd.

Thereafter, the gripping force calculator 73 calculates an estimated gripping force F2 by subtracting the friction force Fd of the sealing member 35 from the theoretical gripping force F1 (F2=F1−Fd). The gripping force calculator 73 further calculates the current gripping force Fc by correcting the estimated gripping force F2 in accordance with the orientation of the robotic forceps 2. Specifically, the gripping force calculator 73 multiplies the estimated gripping force F2 by a correction coefficient α, thereby calculating the current gripping force Fc.

To be more specific for the correction coefficient α, the gripping force calculator 73 acquires information about the orientation of the robotic forceps 2 from the manipulator 10, calculates the orientation of the robotic forceps 2, and calculates the correction coefficient α from the calculated orientation. For example, the correction coefficient α represents the influence of, for instance, reaction force in the gripping direction due to the gravitational force of the gripped object.

Figure 5:
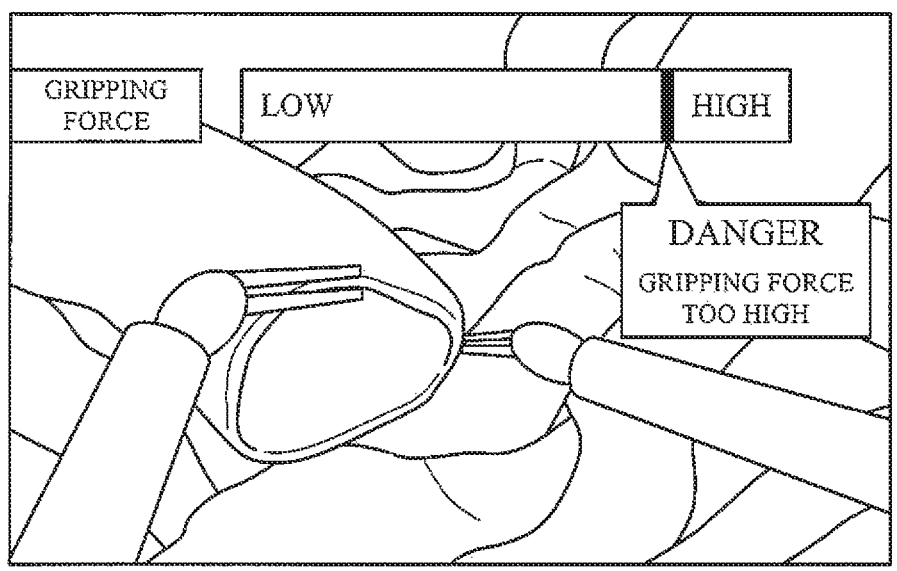
FIG. 5 shows one example of a screen displayed on a monitor.

The calculated current gripping force Fc is transmitted from the gripping force calculator 73 to the monitor 8. As shown in FIG. 5, the monitor 8 displays the current gripping force Fc together with an image of the inside of the body of a patient. In the example shown in FIG. 5, the current gripping force Fc is indicated by an indicator in a gripping force scale. Alternatively, the current gripping force Fc may be displayed only as a numerical value, for example.

The current gripping force Fc calculated by the gripping force calculator 73 is also transmitted to the alarm displayer 74. When the current gripping force Fc exceeds a threshold y, the alarm displayer 74 displays an alarm on the monitor 8. Desirably, the threshold y is set for each type of gripper 24 and each type of organ undergoing the surgery.

As described above, in the hydraulic forceps system 1 of the present embodiment, the current gripping force Fc calculated by the control device 7 is displayed on the monitor 8, and thereby the current gripping force of the gripper 24 can be shown to the doctor operating the robotic forceps 2.

Further, in the present embodiment, the gripping force calculator 73 calculates the current gripping force Fc based on the estimated position $ex_1$ of the first piston derived by the observer 72. This makes it possible to calculate the current gripping force Fc of the gripper 24 by taking into account the position of the first piston 32 without installing a position sensor at the distal end portions of the robotic forceps 2.

Still further, in the present embodiment, the gripping force calculator 73 calculates the friction force Fd of the sealing member 35 disposed between the first piston 32 and the first cylinder 31, and calculates the estimated gripping force F2 by using the calculated friction force Fd. In this manner, the estimated gripping force F2 can be calculated by taking into account the friction force Fd.

Still further, the gripping force calculator 73 calculates the current gripping force Fc by correcting the estimated gripping force F2 in accordance with the orientation of the robotic forceps 2. In this manner, the current gripping force Fc can be calculated by taking into account the orientation of the robotic forceps 2.

Still further, the control device 7 includes the alarm displayer 74. This makes it possible to let the doctor know immediately when the gripping force of the gripper 24 has reached a dangerous level.

(Variations)

The present invention is not limited to the above-described embodiment. Various modifications can be made without departing from the spirit of the present invention.

As one example, instead of the observer 72, which derives the estimated position $ex_1$ of the first piston 32, a position sensor that directly detects the position $x_1$ of the first piston 32 may be provided on the first cylinder 31.

As another example, the control device 7 may calculate the current gripping force Fc of the gripper 24 based solely on the pressure detected by the pressure sensor 61 without based on the position $x_2$ of the second piston 42 detected by using the position sensor 62.

In the above-described embodiment, the current gripping force Fc is calculated by correcting the estimated gripping force F2. However, in a case where the orientation of the robotic forceps 2 does not change much, the estimated gripping force F2 may be directly used as the current gripping force Fc.

When calculating the current gripping force Fc, not only the friction force Fd of the sealing member 35, but also the friction force of the sealing member 45 disposed between the second piston 42 and the second cylinder 41 may be taken into account.

The robotic forceps 2 need not be equipped with the built-in motor 52, and may be operated manually. In this case, the monitor 8 may be set independently in an operating room so that the doctor standing by the patient can see the monitor 8.

In the above-described embodiment, the first piston 32 is moved rearward by the urging force of the spring 34. However, as an alternative, another hydraulic fluid supply/discharge mechanism including the second cylinder 41, the second piston 42, the linear motion mechanism 51, and the motor 52 may be installed; the second pressure chamber 4A of this other hydraulic fluid supply/discharge mechanism may be connected to the back pressure chamber 3B formed between the front wall of the first cylinder 31 and the first piston 32; and the first piston 32 may be moved rearward by the hydraulic pressure of the hydraulic fluid supplied to the back pressure chamber 3B. As another alternative, one end of a wire may be fixed to the first piston 32, and the first piston 32 may be moved rearward by pulling the wire.

As another example, there may be additionally provided means that make it possible to perform correction on the observer 72 in accordance with the state of the first piston 32 and/or the second piston 42, load conditions, individual differences of the robotic forceps 2, surrounding environment, etc.

REFERENCE SIGNS LIST 1 hydraulic forceps system
2 robotic forceps
20 hydraulic fluid
24 gripper
31 first cylinder
32 first piston
3A first pressure chamber
35, 45 sealing member
41 second cylinder
42 second piston
4A second pressure chamber
51 linear motion mechanism
52 motor
61 pressure sensor
62 position sensor
7 control device
72 observer
73 gripping force calculator
74 alarm displayer
8 monitor

The invention claimed is:

1. A hydraulic forceps system comprising:
robotic forceps whose gripper is opened and closed by utilizing hydraulic pressure of a hydraulic fluid, the robotic forceps comprising:
  a first piston coupled to the gripper;
  a first cylinder accommodating the first piston and forming a first pressure chamber together with the first piston, the first pressure chamber being filled with the hydraulic fluid;
  a second piston;
  a second cylinder accommodating the second piston and forming a second pressure chamber together with the second piston, the second pressure chamber being filled with the hydraulic fluid;
  a communication passage through which the first pressure chamber and the second pressure chamber communicate with each other; and
  a motor that drives the second piston via a linear motion mechanism,
a pressure sensor that detects a pressure of the hydraulic fluid;
a control device that calculates a current gripping force of the gripper based on the pressure of the hydraulic fluid detected by the pressure sensor;
a monitor that displays the current gripping force, and
a position sensor configured to detect a position of the second piston, wherein
the control device includes:
  an observer that derives an estimated position of the first piston based on the pressure of the hydraulic fluid detected by the pressure sensor and the position of the second piston detected by using the position sensor; and
  a gripping force calculator that calculates the current gripping force based on the estimated position of the first piston and the pressure of the hydraulic fluid detected by the pressure sensor.

2. The hydraulic forceps system according to claim 1, wherein the monitor displays the current gripping force together with an image of an inside of a body of a patient.

3. The hydraulic forceps system according to claim 2, wherein the gripping force calculator:

calculates a theoretical gripping force from the pressure of the hydraulic fluid detected by the pressure sensor;

calculates a friction force of a sealing member disposed between the first piston and the first cylinder from the estimated position of the first piston and the pressure of the hydraulic fluid detected by the pressure sensor; and calculates an estimated gripping force by subtracting the friction force of the sealing member from the theoretical gripping force.

4. The hydraulic forceps system according to claim 3, wherein the gripping force calculator calculates the current gripping force by correcting the estimated gripping force in accordance with an orientation of the robotic forceps.

5. The hydraulic forceps system according to claim 2, wherein the control device includes an alarm displayer that displays an alarm on the monitor when the current gripping force exceeds a threshold.

6. The hydraulic forceps system according to claim 1, wherein the gripping force calculator:

calculates a theoretical gripping force from the pressure of the hydraulic fluid detected by the pressure sensor;

calculates a friction force of a sealing member disposed between the first piston and the first cylinder from the estimated position of the first piston and the pressure of the hydraulic fluid detected by the pressure sensor; and calculates an estimated gripping force by subtracting the friction force of the sealing member from the theoretical gripping force.

7. The hydraulic forceps system according to claim 6, wherein the gripping force calculator calculates the current gripping force by correcting the estimated gripping force in accordance with an orientation of the robotic forceps.

8. The hydraulic forceps system according to claim 7, wherein the control device includes an alarm displayer that displays an alarm on the monitor when the current gripping force exceeds a threshold.

9. The hydraulic forceps system according to claim 6, wherein the control device includes an alarm displayer that displays an alarm on the monitor when the current gripping force exceeds a threshold.

10. The hydraulic forceps system according to claim 1, wherein the control device includes an alarm displayer that displays an alarm on the monitor when the current gripping force exceeds a threshold.

* * * * *